(12) United States Patent
Bergh (10) Patent No.: US 10,332,054 B2
(45) Date of Patent: Jun. 25, 2019

(54) METHOD, GENERATOR DEVICE, COMPUTER PROGRAM PRODUCT AND SYSTEM FOR GENERATING MEDICAL ADVICE

(75) Inventor: Cecilia Bergh, Stockholm (SE)

(73) Assignee: MANDOMETER AB, Huddinge (SE)

( * ) Notice: Subject to any disclaimer, the term of this patent is extended or adjusted under 35 U.S.C. 154(b) by 2176 days.

(21) Appl. No.: 12/412,434

(22) Filed: Mar. 27, 2009

(65) Prior Publication Data

US 2010/0205006 A1    Aug. 12, 2010

(30) Foreign Application Priority Data

Feb. 9, 2009   (SE) ..................................... 0900156

(51) Int. Cl.
| | |
|---|---|
| *G06Q 50/00* | (2012.01) |
| *G06F 17/30* | (2006.01) |
| *G06Q 10/06* | (2012.01) |
| *G06Q 50/22* | (2018.01) |
| *G06Q 50/24* | (2012.01) |
| *G06F 16/95* | (2019.01) |

(52) U.S. Cl.
CPC ....... *G06Q 10/06375* (2013.01); *G06F 16/95* (2019.01); *G06Q 50/22* (2013.01); *G06Q 50/24* (2013.01)

(58) Field of Classification Search
CPC ........ G06Q 50/22; G06Q 10/10; G06Q 50/24; G16H 10/60; G16H 15/00; G16H 50/30; A61B 5/0002; A61B 5/4094; A61B 2560/0271; G06F 19/325; G06F 19/3418; G06F 19/324; G06F 19/3456; G06F 19/3481

USPC .......................................................... 705/2, 3
See application file for complete search history.

(56) References Cited

U.S. PATENT DOCUMENTS

| | | | |
|---|---|---|---|
| 2004/0260577 A1* | 12/2004 | Dahlin et al. ..................... 705/2 |
| 2007/0192143 A1* | 8/2007 | Krishnan et al. ................. 705/3 |
| 2009/0043608 A1* | 2/2009 | Nadas et al. ...................... 705/3 |
| 2010/0198755 A1* | 8/2010 | Soll et al. ....................... 706/11 |
| 2010/0262045 A1* | 10/2010 | Heaton et al. ................ 600/595 |

* cited by examiner

*Primary Examiner* — Maroun P Kanaan
(74) *Attorney, Agent, or Firm* — Adsero IP (57) ABSTRACT

A medical advice generator device (100) comprising an input unit (102) arranged to receive a query and/or personal data from a patient; an advice generator unit (100*a*) for generation of personalized medical advice to a patient; an output unit (104) arranged to provide a patient with information; said medical advice generator device (100) being arranged to communicate with a first storage (106) to register said personal data entered by the patient; said medical advice generator device being arranged to communicate with a second storage (107) containing health-related data using said query, in order to retrieve a matching response based on a weighted and normalized n-gram similarity function; and modify the matching response using said personal data as well as the patient's history of interaction with the system; and arranged to provide the response to a user display. One of the most important advantages of the present invention is that it provides personalized medical advice which is adapted to the patient's personal needs, e.g. with respect to his/her current mental state or history of interaction with the system.

21 Claims, 9 Drawing Sheets

*Cecilia*

The course of not being able to be inactive and to rest is that when you are active you receive a temporary relief of anxiety. When you are in movement, doing sit-ups or the like, the anxiety disappears for a short while. The problem is that you will not get rid of the anxiety by this manner. You are only postponing it, and soon it will be back again. At the end, the anxiety will return more often in shorter and shorter time span, and you will have to activate yourself more often to feel good, and this encourage the upholding of your illness. The only manner to reverse this is by denying the lust to activate you, and just try to cope with the anxiety when it occurs. Fight against it, and at the end it will be easier to rest.

Logg out

Note Book

Help

METHOD, GENERATOR DEVICE, COMPUTER PROGRAM PRODUCT AND SYSTEM FOR GENERATING MEDICAL ADVICE

RELATED APPLICATION

This application claims priority of Swedish Patent Application No. 0900156-1 filed on Feb. 9, 2009, which application is incorporated herein in its entirety.

TECHNICAL FIELD

The present invention relates to a method, generator device, computer program product and system for generating medical advice.

BACKGROUND

Today, computer-based systems are known which enable patients to receive medical care in their own home, rather than being admitted to a hospital. For instance, the Mandometer® system, comprising a portable computer connected to a scale, can be used to help patients with eating disorders to normalize their eating behaviour. During the course of a meal, the system displays continuous feedback to the patient regarding the consumed amount and eating speed.

However, in addition to this practical eating training, patients with eating disorders have a great need of mental support in order to break their pattern of destructive behaviour. Thus, these patients often have questions or issues that they want to discuss with a medical professional. Unfortunately, doctors are not available to answer questions around the clock, and in any case they tend to have limited time to deal with such questions. The patient's questions can also be complex to the degree that a team of specialists must be consulted, which is expensive and leads to a time delay before an answer can be provided.

Furthermore, patients with eating disorders have a tendency to go over the same questions over and over again, even though they have already received an answer. Such patients need help breaking their compulsive thought patterns.

The need to consult with a medical professional is not restricted to patients with eating disorders, but applies equally to patients suffering from any illness or symptoms showing compulsive thought patterns.

Furthermore, there is an ever increasing demand for generating personalized medical advice for a patient. Because of that demand there have been many different ways developed to do this, for instance medical expert systems are provided where a medical professional can enter a set of symptoms and receive suggestions for a diagnosis. Of course, today there are also virtual medical advisors directed toward patients, such as Internet based sites, for instance medical advice sites. Such sites are suitable for generating general medical advice, but normally suffer from drawbacks in that they are not adapted to the specific needs or characteristics of the patient.

Typically, prior art solutions do not provide medical advice tailored to an individual user with respect to the patient's history of interaction with the system, and his/her current mental state.

For example, in a known system, the patient accesses a web site and is presented with a series of predefined questions and answers. Based on the selected answers, the system then displays medical advice to the patient. In such systems, each patient accessing a certain site is shown the same response though they have different personal characteristics and interaction history. These systems are also limited in that they cannot depart from the predefined sequence of questions, and therefore there is a high risk that any specific question that the patient has cannot be answered, or that the response given is not appropriate, e.g. given the mental state of the patient. Some more sophisticated systems have the capability to change the response after a certain period of time.

Thus, according to our best knowledge, none of the existing techniques present a way suitable for providing personalized medical advice in a targeted way, or providing solutions to the situation described in the previous paragraph, providing a response that is tailored to the patient's current mental state and history of interaction with the system, although already existing infrastructure such as conventional medical treatment Internet sites could possibly support such techniques.

Eating disorders, in the form of anorexia and bulimia nervosa, pose a challenge to society, and gravely affect the lives of many young females.

In particular, though research has been performed over the last fifty years, eating disorders are still by many considered chronic disorders. A recent review of available treatments and bulimia nervosa showed that most conventional employed methods fail to provide any improvement for the patients.

Thus, there is certainly a need to solve also this particular problem.

SUMMARY OF THE INVENTION

The present invention provides a new method for generating personalized medical advice for use in the treatment of eating disorders.

According to a first aspect of the present invention, this is achieved by a method for generating personalized medical advice, which comprises the steps of:

requesting personal data, such as current mental state, from a patient at regular intervals;

registering said personal data in a first storage whenever it is entered by the patient;

receiving a query from the patient by means of an input device;

searching a second storage containing health-related data using said query, in order to retrieve a matching response based on a weighted and normalized n-gram similarity function;

modifying the matching response using said personal data as well as the patient's history of interaction with the system; and providing the response to a user display.

In this way, personalized medical advice in the form of a virtual caregiver could be provided, in particular suitable for use in the treatment of eating disorders According to an embodiment of the invention, the method further comprises the step of providing a personal patient diary comprising a dialogue, a barometer of subject, and a patient's own notes.

According to an embodiment of the present invention, the method further comprises the step of performing, if no matching response is found, at least one additional search using keywords from the query; and retrieving, if there is still no match, a default response from said second storage containing health-related data.

According to embodiment of the present invention, the method further comprises the step of checking, in a first storage containing the patient's interaction history, if the same or similar question has been asked more than a predetermined number of times, and, if this is the case, modifying the response so that it no longer contains an answer to the question.

According to embodiment of the present invention, the method further comprises the step of monitoring the patient's mental state, for instance, by displaying an "emotional meter" to the patient.

The invention further provides a device for generating personalized medical advice, in particular suitable for use in the treatment of eating disorders.

According to a second aspect of the present invention, this is achieved by a medical advice generator device comprising:

an input unit arranged to receive a query and/or personal data from a patient;
an advice generator unit for generation of personalized medical advice to a patient;
an output unit arranged to provide a patient with information;
said medical advice generator device being arranged to communicate with a first storage to register said personal data entered by the patient;
said medical advice generator device being arranged to communicate with a second storage containing health-related data using said query, in order to retrieve a matching response based on a weighted and normalized n-gram similarity function; and modify the matching response using said personal data as well as the user's history of interaction with the system; and arranged to provide the response to a user display.

According to an embodiment of the present invention, the advice generator is arranged to have access to a first storage, containing personal data concerning the patient. Typically, the first storage comprises data regarding the patient's mental state and history of interaction with the system.

According to an embodiment of the present invention, the medical advice generator further comprises a personal patient diary comprising a dialogue, a barometer of subject, and a patient's own notes.

According to an embodiment of the present invention, the medical advice generator is arranged to have access to a second storage, containing medical information.

Typically, this information is based on a large number of questions collected from medical personnel and patients at the clinic, as well as chat sessions between patients and their caretakers. Typically, the answers used in the database are written by chief medical personnel.

According to an embodiment of the present invention, the advice generator is arranged to be continuously updated as the patient interacts with the system.

According to an embodiment of the present invention, the first and second storages reside locally in a server, which at least partly comprises the medical advice generator.

According to a third aspect of the present invention, there is provided a computer program product for generating personalized medical advice, in particular suitable for use in the treatment of eating disorders. The computer program product comprises computer-readable code portions, comprising: an executable portion capable of providing a client application by a client comprising the steps of:

requesting personal data, such as current mental state, from a patient at regular intervals;
registering said personal data in a first storage whenever it is entered by the patient;
receiving a query from the patient by means of an input device;
searching a second storage containing health-related data using said query, in order to retrieve a matching response based on a weighted and normalized n-gram similarity function;
modifying the matching response using said personal data as well as the patient's history of interaction with the system; and
providing the response to a user display. It is appreciated that the computer program product is adapted to perform all embodiments relating to the above described method, as is apparent from the attached set of dependent system claims.

The present invention also relates to a system for generating personalized medical advice, in particular suitable for use in the treatment of eating disorders. This system comprises at least one medical advice generator device comprising:

a first storage arranged to register personal data entered by a patient;
an input device arranged to receive a query from a patient;
said medical advice generator device being arranged to search a second storage containing health-related data using said query, in order to retrieve a matching response based on a weighted and normalized n-gram similarity function; and modify the matching response using said personal data as well as the user's history of interaction with the system; and
provide the response to a user display.

According to a principal aspect of the present invention, there is provided a question answering system, embodied as a virtual caregiver, accessible through a web interface. Questions are posed to the system using written natural language. In this way, the invention supports a more natural feeling dialogue and promotes user's trust in the answers.

In this disclosure, the term "medical advice generator" is used. Herein, "medical advice generator" is defined as a generator including or providing an application for generating personalized "medical" advice, or the like. This means that the term "medical" is to be interpreted broadly, i.e. also including more than strictly "medical" advice. Also the term patient is intended to be any kind of user having the same or similar needs as a patient. The advice generator may be embodied as hardware combined with software, or alternatively embodied as a computer program product that can be run on a compatible computer, which may be located in another device communicating with the medical advice generator device; thus for instance the medical advice generator device may be located in a plug-in card that communicates with another device provided with suitable hardware such as a processor together providing the application for generating personalized medical advice. In this case the medical advice generator device is embodied as software that can be run on any thereto compatible computer, of which the latter is well-known per se.

An advantage is that it provides personalized medical advice which is adapted to the patient's personal needs, e.g. with respect to his/her current mental state or history of interaction with the system. This is made possible by the built-in flexibility of the query matching process based on matching of user's questions with database entries using a weighted and normalized n-gram similarity function.

Another advantage is to provide to answer more complex questions than in known solutions. This is made possible by the built-in flexibility of the query matching process, and also because of, for instance the medical advice generator has access to several information sources.

Yet another advantage is that the advice generator is always able to supply advice which is up-to-date with current research or practice. This is achieved by providing connections to information sources available over the Internet, such as public discussion forums, which are continuously being updated.

Additional features and advantages are disclosed by the appended dependent claims.

BRIEF DESCRIPTION OF THE DRAWINGS

To further explain the invention, embodiments chosen as examples will now be described in greater details with reference to the drawings of which.

DETAILED DESCRIPTION OF THE INVENTION

Figure 1:
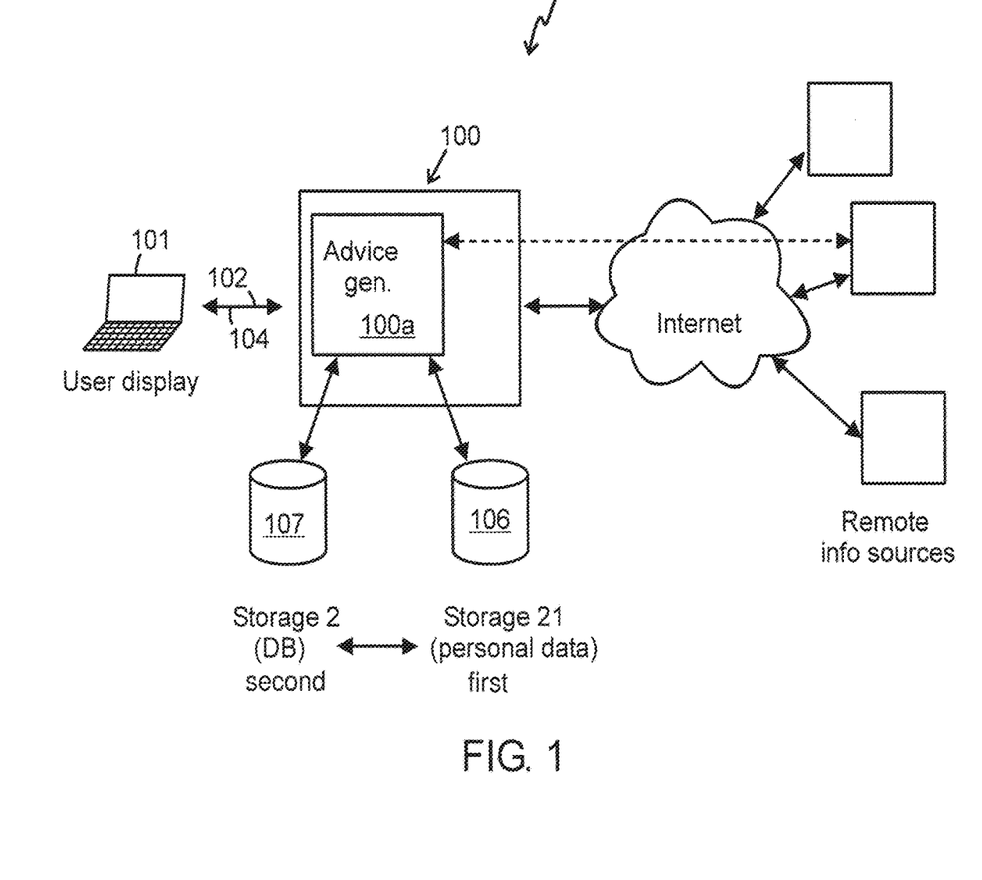
FIGS. 1 and 2, respectively, is an illustration of a system for generating personalized medical advice according to an embodiment of the present invention. The system includes a medical advice generator device and a user display.
Figure 2:
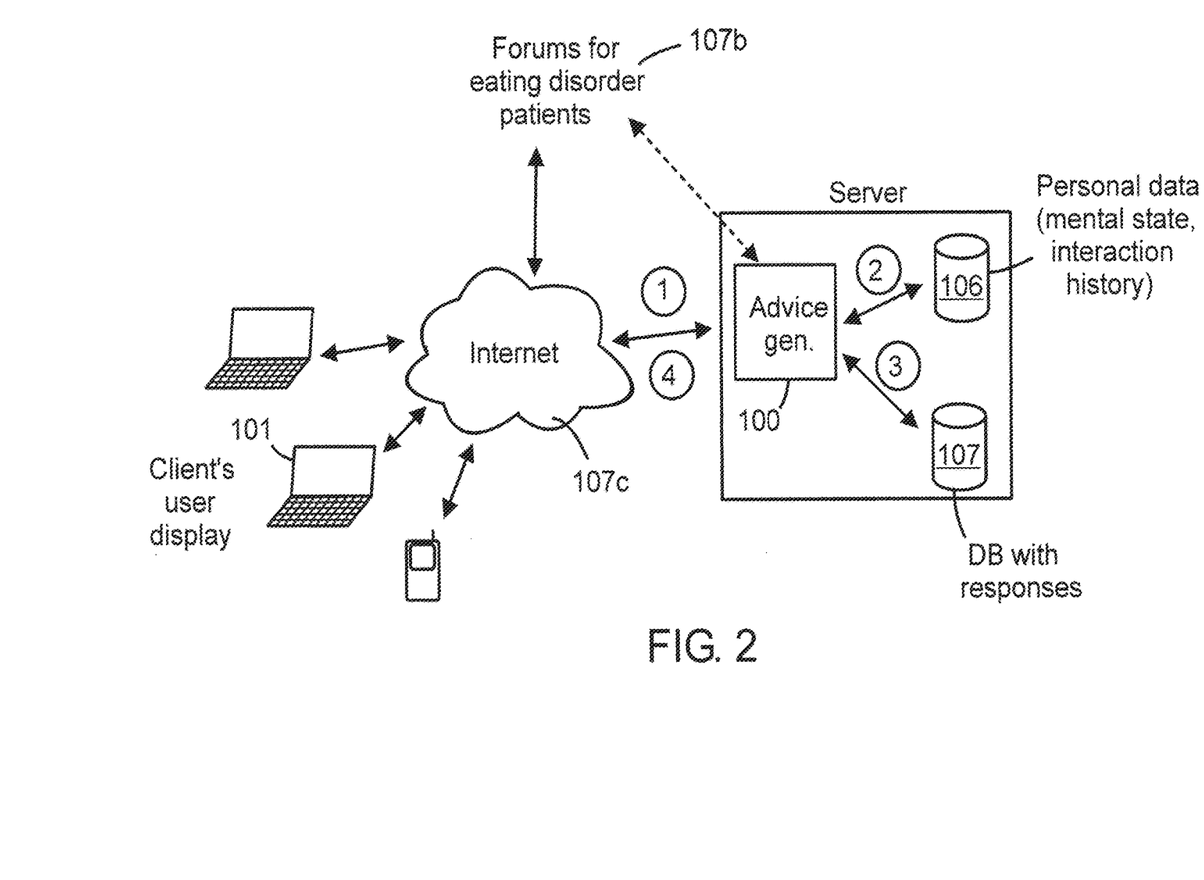

Referring now to FIGS. 1 and 2, there is illustrated a system 10 for generating medical advice according to an embodiment of the present invention. The system 10 illustrated in FIG. 1 includes a medical advice generator device 100. Typically, the medical advice generator 100 comprises an advice generator unit 100a and is implemented by means of a portable or stationary computer located in the patient's home environment, wherein the computer comprises a user display 101 for presenting information to a user, typically a patient. FIG. 1 illustrates a computer with a user display 101, which computer may be portable or stationary, connectable to the Internet and arranged for such communication, but any suitable implementation such as implementation in another type of suitable portable communication device, for instance a Personal Digital Assistant (PDA) is also possible.

As illustrated in FIG. 1, the medical advice generator 100, comprises an input unit 102 for receiving input from a patient (not illustrated), and an output unit 104 for providing information to a user display 101. The input/output units 102, 104 may be located in the user display 101 and may be combined into one dual unit. Because of this, the input/output units 102, 104 are schematically indicated as a double-headed arrow intending to illustrate the dual functionality thereof.

The medical advice generator 100 also has access to a first storage 106, for instance a database, containing personal data concerning the patient. Typically, the first storage 106 comprises data regarding the patient's mental state and history of interaction with the system. Thus, typically this first storage 106 is continuously updated as the patient interacts with the system. The gathering of this data will be further explained below.

Additionally, or alternatively, it is also possible to store other types of information such as the age, weight, sex and the complete medical history of the patient.

Furthermore, the medical advice generator 100 also has access to a second storage 107, also in the form of a data-base, or a similar type of data source, containing medical information. Typically, this information is based on a large number of questions collected from medical personnel and patients at the clinic, as well as chat sessions between patients and their caretakers. Also other information sources may be employed to provide information to the second storage 107. This is illustrated in a simplified way indicated "remote info sources". Typically, the answers used in the database 107 are written by chief medical personnel at the clinic to provide as proper answers as possible. In addition, or alternatively, to be able to perform more complex matching, the database 107 also uses keywords that are linked to particular answers in the database 107.

Typically, the invention is embodied as a question answering system, embodied as a virtual caregiver, accessible through a web interface. Typically, matching of user's questions with database entries is performed using a weighted and normalized n-gram similarity function. Also other types of representations that handle morphological variation, spelling errors and compound words could be employed. String similarity measurements such as Levenstein distance is known for spelling correction and handles morphological variation but is less suitable because of the presence of compound words in typical questions and answers. Furthermore, it is only useful on the word level and cannot make use of word order information, which may be useful in the invention.

In general, character based n-gram similarity measures form a family of similarity measures that handles morphological variation, spelling errors and compound words and can make use of word order Herein, we refer to n-grams as a type of probabilistic model for predicting the next item in a sequence. N-grams per se are known and are used in genetic sequence analysis for instance.

Herein, we refer to an n-gram as a sub-sequence of n items from a given sequence. The items can for instance be letters or words according to the application.

Questions are posed to the system using written natural language. By providing a virtual caregiver, the hope is to support a more natural feeling dialogue and to promote user's trust in the answers. The aim of the invention is according to an aspect, to be able to answer and confirm patients at times when a human caregiver is not available. Furthermore, by leveraging body language and facial expressions, the degree of solemnity of the issues discussed can be conveyed across several modalities. In addition, it is hoped that the virtual caregiver will be more interesting and fun to use, lessening the focus on the patient's problems.

Now is referred to FIG. 2. The first and second storages 106, 107, may alternatively reside locally in a server, "SERVER", which at least partly comprises and/or provides the medical advice generator 100. The communication lines between the medical advice generator 100 and storages 106, 107, also herein illustrated as data-bases, or other sources of information (not shown), could be any suitable such as cable connections combined with wireless applications, for instance wireless gateway/switches and a TCP/IP based network.

Typically, the medical advice generator 100 is also connectable to one or more public forums 107b via the Internet, such as forums for eating disorder patients, and may use information from these forums to construct answers to questions posed by the user.

The medical advice generator 100 could also be provided with circuitry and computer programs to provide programming or updating of the medical advice generator, also automatically, e.g. using an Internet connection 107c.

The medical advice generator 100 is typically also provided with access to a vocabulary containing terminology commonly used in the field of eating disorders.

In an alternative embodiment of the present invention, a Palm Pilot device or similar PDA device is programmed to receive input from its serial port attached to a medical advice generator.

The PDA device may be programmed with software to co-operate with the inventive medical advice generator or alternatively, the inventive medical advice generator could be provided as a pure software-solution that is downloaded in the Palm Pilot device or the PDA.

Figure 3:
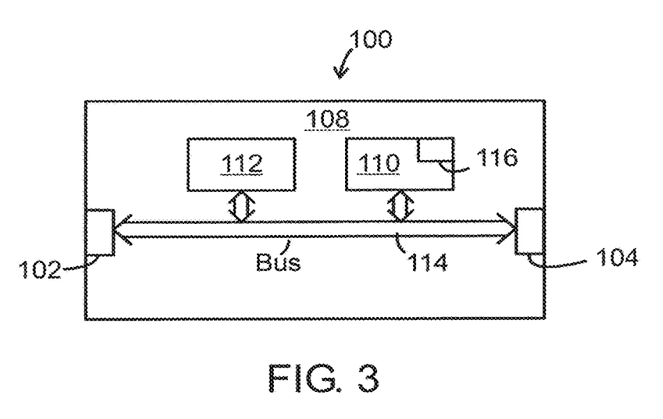
FIG. 3 is an illustration of a block schematic of the medical advice generator according to an embodiment of the present invention.

Now is referred to FIG. 3, which is an illustration of a block schematic of a medical advice generator 100, according to a preferred embodiment of the present invention. The medical advice generator 100 comprises a first input/transmission unit 102 for transmission of data. This first input/transmission unit 102 could be of any conventional type including input/output elements for receiving and transmitting video, audio and data signals wirelessly. Typically, the first transmission unit 102 includes conventional circuitry (not shown) for communication. However, the present invention is by no means limited to the Internet, or any wired communication, but also other wireless communication such as mobile telephone technology, NMT, GSM, 3-G, Bluetooth, W-LAN, ir etc could be employed instead. The medical advice generator 100 also comprises a second output/transmission unit 104 for transmission of said processed signals comprising processed information to a presentation unit, typically a user display (not shown). Located between these two units 102, 104 there is provided a control system 108 arranged to process the patient information.

Typically, this control system 108 comprises a processor 110 connected to a computer memory 112 with a system bus 114, in which memory 112 reside computer-executable instructions 116 for execution; the processor 110 being operative to execute the computer-executable instructions 116 to perform all method steps as will be described below. Interfaces, communication protocols etc required for receiving input from and interacting with an operator will not be described in more detail since this is conventional technology per se and therefore obvious for a person skilled in the art of electronics and computer science to design.

Figure 4:
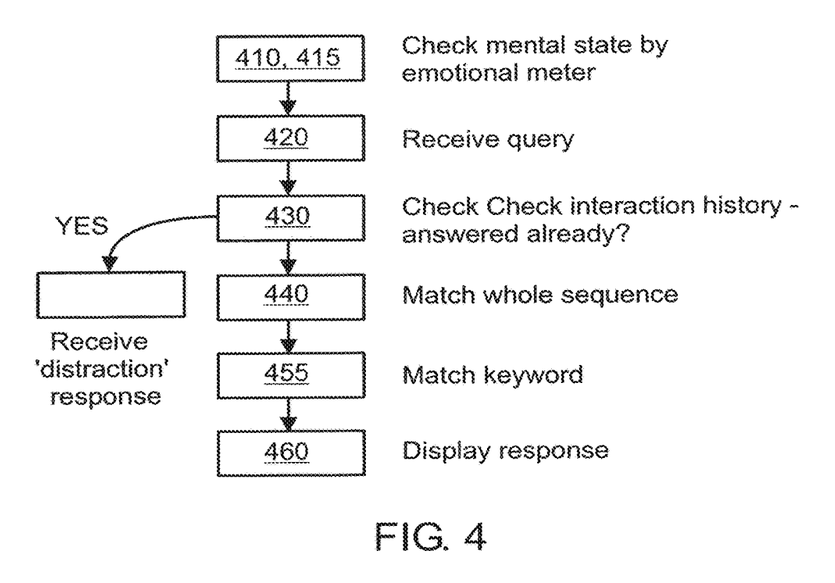
FIG. 4 is an illustration of a flow chart of a method for generating personalized medical advice according to an embodiment of the present invention.

Referring now to FIG. 4, there is shown a flow chart of a method for generating medical advice information according to an embodiment of the present invention. The method corresponds to what have already been disclosed above related to the medical advice generator and the system comprising the same medical advice generator. It is also referred once again to FIGS. 1-2.

Typically, the medical advice generator application continuously monitors the patient's mental state. This is done, for instance, by displaying an "emotional meter" to the patient. At regular intervals, the patient is requested to indicate his/her current mood by marking the appropriate place on the meter, step 410. Typically, this data is saved and is used both to show the patient how his/her mood has varied over time, and to vary the behaviour of the virtual characters (including the virtual caretaker, as will be further described below). In FIG. 4 this is illustrated as a first optional step, including requesting personal data, such as current mental state, from a patient at regular intervals, step 410; including registering said personal data in a first storage whenever it is entered by the patient, step 415;

Thus, typically, the system will also take the patient's mental state into account when preparing an answer, as indicated by the patient using the emotional meter. Thus, a patient feeling depressed may receive responses more directed toward comfort and support.

In a second step 420, the medical advice generator will receive a question in the form of a character string typed in by the user (e.g. "How can I handle a binge eating attack during the weekend?"). This question is forwarded to the medical advice generator 100 by means of the input unit.

In the particular embodiment with the virtual caregiver, the same will strike up a conversation as the patient approaches, e.g. by saying "Is there anything you would like to ask?". The patient can enter a question using their keyboard, for instance "How can I avoid a binge eating attack during the weekend?". This corresponds to the second step, "receiving a query", step 420, illustrated in FIG. 4, The system will then access its associated medical database 107 (See FIG. 1a-b), along with remote sources such as Internet chat forums 107b, to attempt to find a matching answer to the question, step 440 in FIG. 4. The answer will then be displayed to the patient, e.g.: "By setting your alarm at 8.00 each morning, strictly following your meal schedule and never skipping a meal", step 455, "displaying a response" in FIG. 4.

The system also saves information regarding the question and answer, as part of the user's interaction history, step 430 in FIG. 4. Thus, the next time the patient asks the same question, the system will check the interaction history and note that this is the second time the question is asked. The first few, the virtual caretaker will supply the same answer. However, if the patient keeps coming back to the same issue, the system will no longer answer that particular question. Instead, the virtual caretaker will attempt to divert the patient by bringing up a different subject, or by encouraging the patient to do something else.

Typically, the advice generator will check the user's interaction history, using the second storage means, to see if the question has already been asked. If the number of times the question has been asked exceeds a predetermined number (e.g. 3), the advice generator will deduce that the question should not be answered again. Instead, the advice generator will retrieve an appropriate distracting response from the database, step 430. In the next step, step 440, the advice generator will access the patient's personal data, including current mental state, and use it to modify the response if necessary. The response will then be displayed to the user in the next step, step 460.

As an example, if the patient is in a generally stable mental state, the distracting response might read "We have already discussed this a few times. Why don't you go watch our new movie instead?". However, if the patient has indicated feeling sad or depressed, the response may be modified to "I know that you're feeling bad, but I know you can do this! I think you might feel better if you watched a movie instead."

If the question has never been asked, or only asked a few times before, the advice generator will move through steps 440 to 460 trying to find a response.

In step 440, the advice generator will perform a query using the exact wording of the patient's question. The query will be sent to the first information storage means and to any available external data sources. If a match is found, the advice generator will go through steps 440-460 to display an appropriate response. If no match was found, the advice generator will go on to extract keywords from the question in step 455. Another attempt for a match will then be performed using the keywords.

Finally, if no match has been found, the system will use one of a number of default responses (step 460), such as "I understand your concern, but I don't have an answer right now. If you are worried, please call your doctor directly."

Now is also referred to FIG. 5*a-d*, which show an example of a graphical user interface presented to the patient, in the form of a virtual meeting room. This virtual meeting room represents a form of a "virtual clinic" which provides an opportunity to chat with treating personnel at a real-world clinic and to pose questions to a "virtual caretaker", herein denoted Dr. Cecilia, see for instance FIG. 5*a* for an example of a dialogue, where the dialogue is presented by citation marks.

Figure 5A:
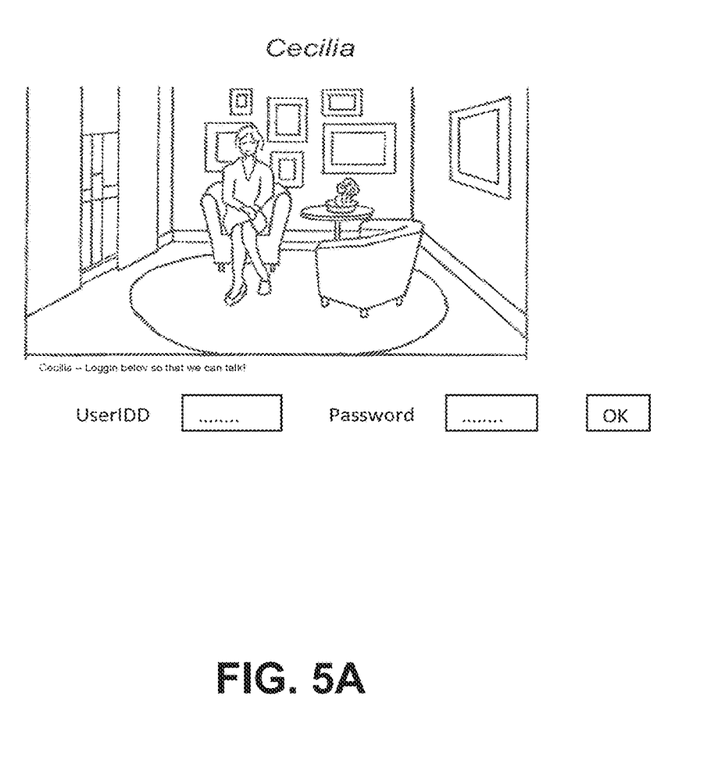
FIGS. 5a-d show an example of the output unit in the form of a graphical user interface presented to the patient, in the form of a virtual world, of which FIG. 5a for instance shows the present invention according to an embodiment, wherein a conversational caregiver, called Dr. Cecilia is provided.

Cecilia: "Please, log-in for a chat". The patient can access the virtual room from any computer or portable communication device by means of a communication network, any time, 24 hours. Typically, the invention is based on the Internet even if Internet access might be a limiting factor. Typically, the aim of the present invention is by no means to replace human caregivers. Instead, typically the present invention aims to be a complementary part of the treatment, solving problems which human caregivers cannot solve. Internet based treatments are known per se. Typically, the present invention could be implemented also in already present medical data base infrastructure.

The primary communication channel used in the system is written text. Users interact with Dr. Cecilia by posing questions using natural language entered using a standard text-field. If the posed question has a sufficiently high similarity with a question in the database, compared to an empirically determined threshold value, the answer is presented directly to the user by Dr. Cecilia. If no such question is found, a certain maximum number, say up to three questions from the database are presented to the user, who can then choose to read the answer to one of the alternatives or to ask another question. An empirically determined lower threshold is used to filter out questions that are unlikely to match the user's question. Since a specific topic often has several different, but highly related, questions and answers, most of the time the reason for presenting more than one answer is that the question posed by the user is in some way underspecified with respect to the questions in the database.

Typically, in general, questions related to the psychological state of the patient, are secondary to the physical condition of the patient and the patient's eating behaviour is the cause of his/her psychological state. The primary focus in the treatment should thus be on teaching the patients how to eat again. By focusing on providing answers to questions related to the disorder, based on scientific facts and expressed in a professional, encouraging, motivating and empathetic language, the hope is that the system will help in disrupting the often ruminating questions and thoughts of the patients.

Figure 5B:
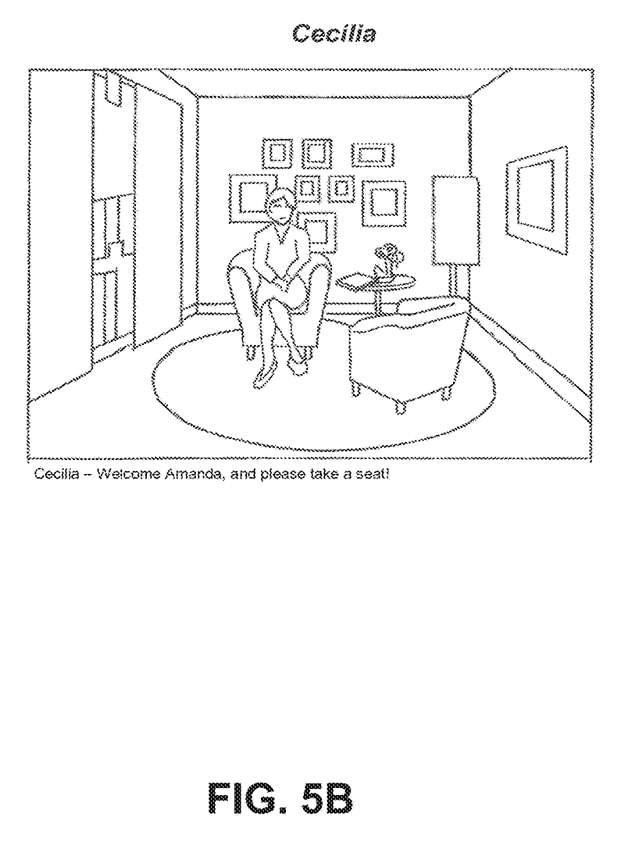
Figure 5C:
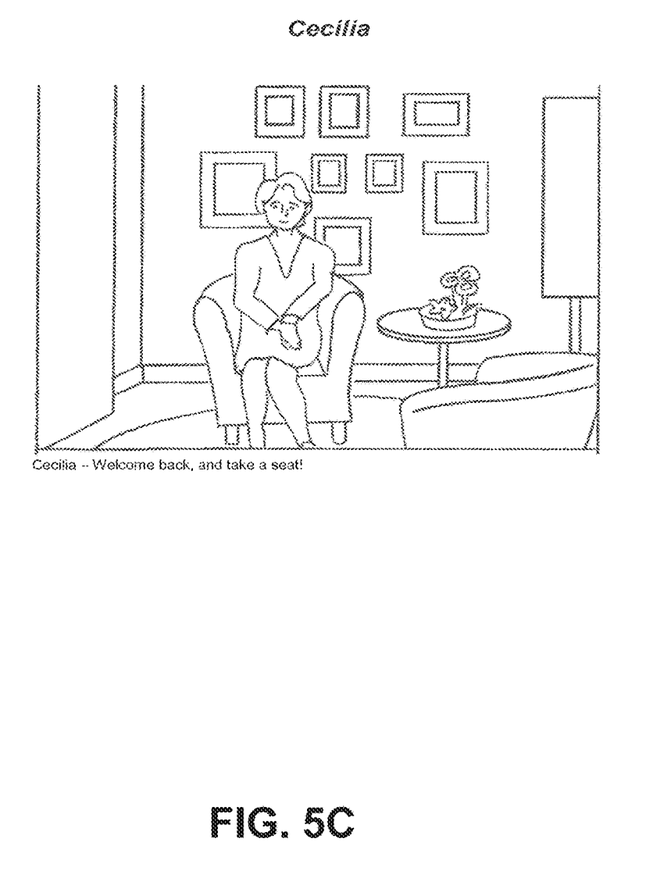
Figure 5D:
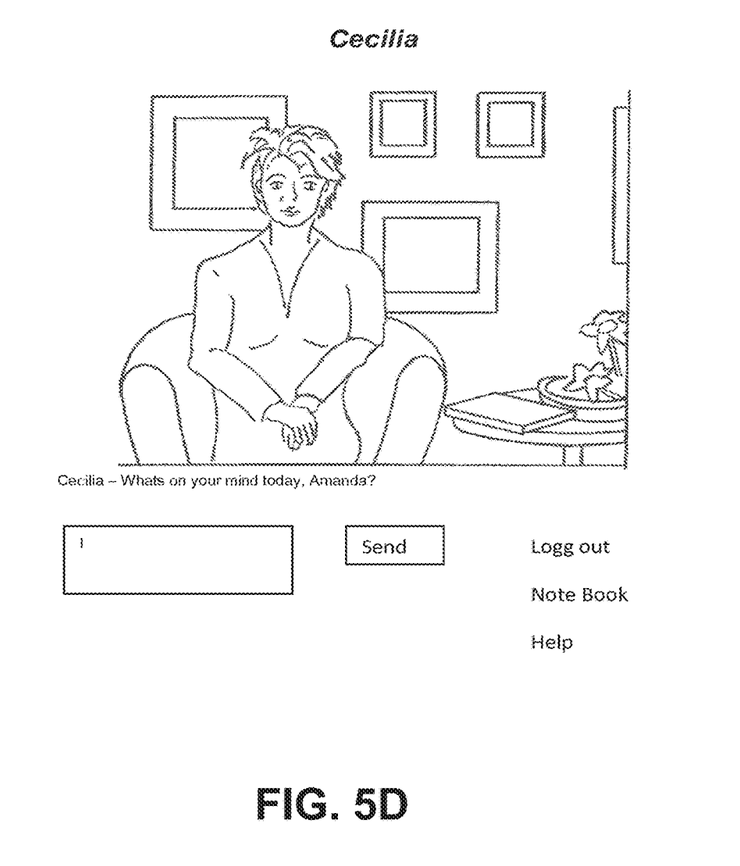
Figure 5E:
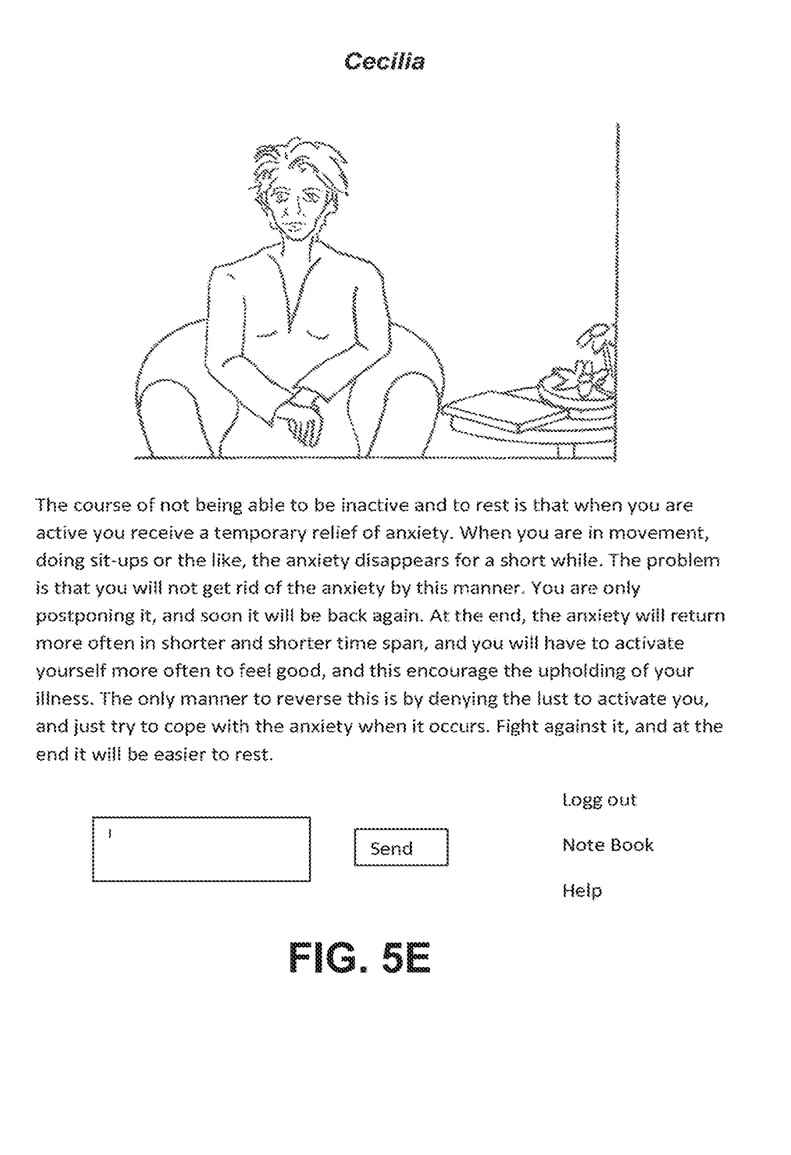

Now is referred to FIG. 5*a-b* showing the present invention according to an embodiment, wherein a conversational caregiver, called Dr. Cecilia is provided.

When the patient starts the virtual room application to chat with Dr. Cecilia, a three-dimensional virtual meeting room will be displayed comprising chairs, in which one chair doctor Cecilia, is sitting ready to give medical advice to the patient (in this case a patient called Amanda), typically similar to a real-world situation; Cecilia: "Welcome back Amanda, please take a seat!", FIG. 5*b*. Doctor Cecilia then asks if there are some questions that Amanda needs to have an answer to. Cecilia: "Is there something special you are wondering about, Amanda?", FIG. 5*c-d*.

As already discussed, patients with eating disorders are not easily motivated and need constantly to be reminded of and encouraged to as why they should stay in treatment. Numerous studies have shown that these aspects are not easily conveyed through written text alone, or by a human caregiver. For example, internal states of the system can be conveyed more directly, by use of facial expressions and body gestures, than is possible with text alone. This is accomplished by the invention.

Studies have also shown that by using friendly small talk, verbal and non-verbal expressions of emotion and expression of emotion and expressions can be conveyed. Furthermore, by using artificial characters, such as Dr. Cecilia, a sense of confidence, which ca have motivational effects can be conveyed.

This is only an example of how to implement the invention and is by no means intended to be limiting in any sense.

Figure 6:
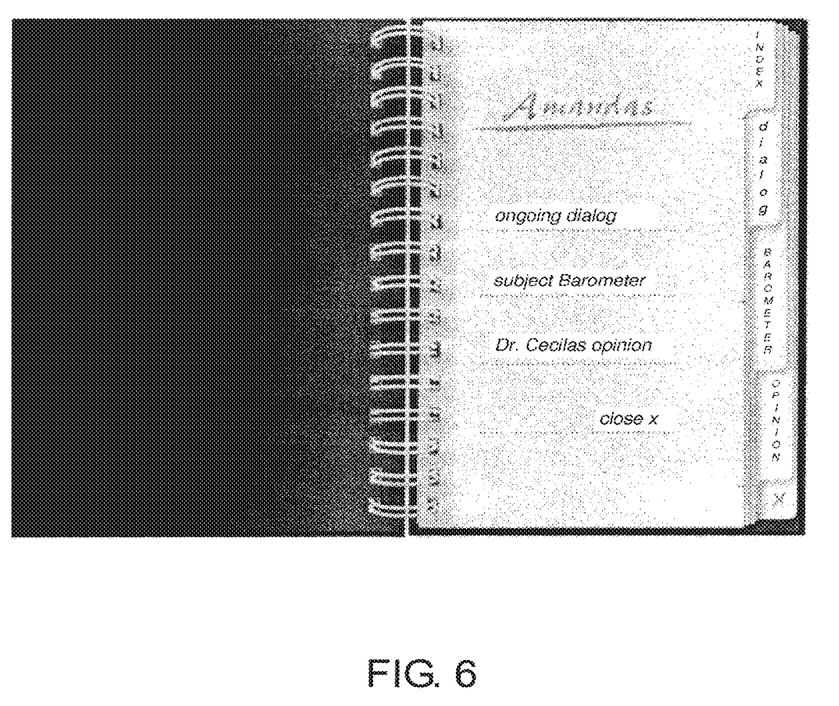
FIG. 6 shows a diary showing a graphical representation of the user's topic history for a time period, say two last weeks.

Typically, all of this could be provided by means of a diary, FIG. 6.

Thus, patients interact with Dr. Cecilia using natural language entered using a standard text field. If the posed question has sufficiently high similarity with a question in the database, compared to an empirically determined threshold value, the answer is presented directly to the patient via the user display by Dr Cecilia. If no such question could be found, up to three questions from the database are presented to the user, who can then choose to read the answer to one of the alternatives or to ask another question. An empirically lower threshold is used to filter out questions that are unlikely to match the user's question. Since a specific topic often has several different, but highly related, questions and answers, most of the time the reason for presenting more than one answer is that the question posed by the user is in some way underspecified with respect to the question in the database.

After each session, the user is provided with a rating from a scale of 1-3 "stars" and a written (pre-formulated) assessment of treatment progress. Each category of questions is assigned a degree of severity in terms of how far the patient is considered to be from remission if she asks questions in this category. The rating of the patient's progress is calculated based on which categories of questions have been in focus during the session. The user can also see, in the form of a bar chart, which categories she has asked most questions about. This allows the patient to keep track of her own development towards recovery and gives her positive and negative feedback. This kind of feedback is an integral part of the treatment method on which the invention is based.

An area of application for the present invention is 24 hour medical advice for weight-control, for instance, whereby a patient could be presented relevant medical information. This is however only a non-limiting example of a typical application.

As will be further explained below, the medical advice generator device could be provided as a computer program product (referred to as a medical advice generator application) that can be executed by a computer. This computer program product could be stored on a record carrier such as a USB, or be downloaded from the Internet. This is not shown in any drawing figure, since the operating principle could easily be derived from the disclosure of the medical advice generator device in FIG. 3 as explained above.

The medical advice generator application may be downloadable as a consequence of other processes. Furthermore, the medical advice generator application may be activated either manually or automatically, and can be run from a remote location such as the web-server in a way known per se.

Throughout this description, the embodiments shown and described should be considered as examples, rather than limitations of the invention. It is to be understood that, when reference is made in this disclosure to the term "display" this refers generically either to a display screen on its own or to the screen and an associated housing, drive circuitry and possibly a physical supporting structure, of which all, or part of is provided for displaying patient information.

All of this is obvious for a person skilled in the art of electronics and/or computer science to perform and/or implement, based on the information already given in this context. Thus, this will not be described in more detail. Any suitable computer language and/or electronics could be employed fore this purpose.

What is claimed is:

1. A computer-implemented method for generating personalized medical advice regarding an eating behaviour for a person seeking answers to the eating behaviour through an Internet portal, the method comprising:
    using an electronic processing to request personal data through the Internet portal from a person who has logged onto the Internet portal by way of an input unit, the personal data including the person's current emotional state of mind, wherein the request comprises a request for the person to indicate the person's current emotional state by means of an onscreen emotional meter having a range scale;
    registering the personal data in a first electronic storage whenever the personal data is entered by the person;
    receiving an eating behaviour query from the person by means of the Internet portal;
    searching a second electronic storage containing health-related data using the query, in order to retrieve a matching response based on a weighted and normalized n-gram similarity function;
    modifying, by the electronic processing device, the matching response using the personal data as well as a person's history of interaction with the electronic processing device to generate a modified matching response; and
    providing, to the person, the personalized medical advice regarding the eating behaviour, based on the modified matching response, via the Internet portal, for display on a display associated with the input unit.

2. The method of claim 1, further comprising:
    storing a personal diary having a dialogue, a barometer of the person, and notes supplied by the person.

3. The method of claim 2, wherein modifying the matching response comprises checking, in the patient's history of interaction with the electronic processing device, if the same or similar question has been asked more than a predetermined number of times, and, if this is the case, modifying the response so that it no longer contains an answer to the question.

4. The method of claim 1, further comprising saving the query and modified matching response in the electronic storage containing the person's interaction history.

5. The method of claim 1, wherein the current emotional state is requested from the person at regular intervals.

6. The method of claim 1, further comprising retrieving a distracting response from the database.

7. The method of claim 1, wherein the first and second electronic storages reside locally in the electronic processing system.

8. A computer system for generating personalized medical advice regarding an eating behaviour for a person seeking answers to the eating behaviour through an Internet portal, the computer system comprising:
    a processor; and
    a non-transitory computer-readable medium containing computer-readable code executable by the processor to cause the computer system to:
        request, through the Internet portal, personal data from a person who has logged onto the Internet portal by way of an input unit, the personal data including the person's current emotional state of mind, wherein the request comprises a request for the person to indicate the person's current emotional state by means of an onscreen emotional meter having a range scale;
        register the personal data in a first electronic storage whenever the personal data is entered by the person;
        receive an eating behaviour query from the person by means of the Internet portal;
        search a second electronic storage containing health-related data using the query, in order to retrieve a matching response based on a weighted and normalized n-gram similarity function;
        modify the matching response using the personal data as well as a person's history of interaction with the computer system to generate a modified matching response; and
        provide to the person, the personalized medical advice regarding the eating behaviour, based on the modified matching-response, via the Internet portal, for display on a display associated with the input unit.

9. The computer system of claim 8, wherein the computer readable code is further executable by the processor to cause the computer system to:
    store a personal diary having a dialogue, a barometer of the person, and notes supplied by the person.

10. The computer system of claim 8, wherein modifying the matching response comprises checking, in the patient's history of interaction with the electronic processing device, if the same or similar question has been asked more than a predetermined number of times, and, if this is the case, modifying the response so that it no longer contains an answer to the question.

11. The computer system of claim 8, wherein the computer readable code is further executable by the processor to cause the computer system to:
    save the query and modified matching response in the electronic storage containing the person's interaction history.

12. The computer system of claim 8, wherein the current emotional state is requested from the person at regular intervals.

13. The computer system of claim 8, wherein the computer readable code is further executable by the processor to cause the computer system to:
    retrieve a distracting response from the database.

14. The computer system of claim 8, further comprising the first and second electronic storages.

15. A non-transitory computer-readable medium for generating personalized medical advice regarding an eating behaviour for a person seeking answers to the eating behaviour through an Internet portal, the medium containing computer-readable code executable by a processor to cause a computer system to:

request, through the Internet portal, personal data from a person who has logged onto the Internet portal by way of an input unit, the personal data including the person's current emotional state of mind, wherein the request comprises a request for the person to indicate the person's current emotional state by means of an onscreen emotional meter having a range scale;

register the personal data in a first electronic storage whenever the personal data is entered by the person;

receive an eating behaviour query from the person by means of the Internet portal;

search a second electronic storage containing health-related data using the query, in order to retrieve a matching response based on a weighted and normalized n-gram similarity function;

modify the matching response using the personal data as well as a person's history of interaction with the computer system to generate a modified matching response; and     provide to the person, the personalized medical advice regarding the eating behaviour, based on the modified matching-response, via the Internet portal, for display on a display associated with the input unit.

16. The non-transitory computer-readable medium of claim 15, wherein the computer readable code is further executable by the processor to cause the computer system to: store a personal diary having a dialogue, a barometer of the person, and notes supplied by the person.

17. The non-transitory computer-readable medium of claim 15, wherein modifying the matching response comprises checking, in the patient's history of interaction with the electronic processing device, if the same or similar question has been asked more than a predetermined number of times, and, if this is the case, modifying the response so that it no longer contains an answer to the question.

18. The non-transitory computer-readable medium of claim 15, wherein the computer readable code is further executable by the processor to cause the computer system to:

save the query and modified matching response in the electronic storage containing the person's interaction history.

19. The non-transitory computer-readable medium of claim 15, wherein the current emotional state is requested from the person at regular intervals.

20. The non-transitory computer-readable medium of claim 15, wherein the computer readable code is further executable by the processor to cause the computer system to:

retrieve a distracting response from the database.

21. The non-transitory computer-readable medium of claim 15, wherein the computer system comprises the first and second electronic storages.

\* \* \* \* \*

UNITED STATES PATENT AND TRADEMARK OFFICE
CERTIFICATE OF CORRECTION

PATENT NO. : 10,332,054 B2  
APPLICATION NO. : 12/412434  
DATED : June 25, 2019  
INVENTOR(S) : Cecilia Bergh et al.

Page 1 of 1

It is certified that error appears in the above-identified patent and that said Letters Patent is hereby corrected as shown below:

On the Title Page (75) Inventors should read as:  
Cecilia Bergh, Stockholm (SE)  
Per Södersten, Stockholm (SE)

Signed and Sealed this  
Sixth Day of October, 2020

Andrei Iancu  
*Director of the United States Patent and Trademark Office*